US008834553B2

(12) United States Patent
Melanson et al.

(10) Patent No.: US 8,834,553 B2
(45) Date of Patent: Sep. 16, 2014

(54) ANCHORS WITH BIODEGRADABLE CONSTRAINTS

(75) Inventors: David A. Melanson, Hudson, NH (US); Christopher Nutting, Newtonville, MA (US); Barry Maxwell, Spencer, MA (US); Peter Shank, Boylston, MA (US); John Panek, Peabody, MA (US)

(73) Assignee: GI Dynamics, Inc., Lexington, MA (US)

( * ) Notice: Subject to any disclaimer, the term of this patent is extended or adjusted under 35 U.S.C. 154(b) by 392 days.

(21) Appl. No.: 13/045,363

(22) Filed: Mar. 10, 2011

(65) Prior Publication Data

US 2011/0276091 A1 Nov. 10, 2011

Related U.S. Application Data

(63) Continuation-in-part of application No. PCT/US2010/048444, filed on Sep. 10, 2010.

(60) Provisional application No. 61/276,381, filed on Sep. 11, 2009, provisional application No. 61/361,806, filed on Jul. 6, 2010.

(51) Int. Cl.
| A61F 2/06 | (2013.01) |
| A61F 2/04 | (2013.01) |
| A61F 5/00 | (2006.01) |
| A61F 2/848 | (2013.01) |

(52) U.S. Cl.
CPC ........... *A61F 2/04* (2013.01); *A61F 2220/0016* (2013.01); *A61F 5/0076* (2013.01); *A61F 2002/045* (2013.01); *A61F 2002/8483* (2013.01); *A61F 2250/0031* (2013.01)
USPC ........................... 623/1.14; 606/232; 606/151

(58) Field of Classification Search
USPC ........................................................ 623/1.14
See application file for complete search history.

(56) References Cited

U.S. PATENT DOCUMENTS

| 4,258,724 A | 3/1981 | Balat et al. |
| 4,616,439 A | 10/1986 | Lee |

(Continued)

FOREIGN PATENT DOCUMENTS

| DE | 10125999 A1 | 11/2002 |
| EP | 0 701 800 A1 | 3/1996 |

(Continued)

OTHER PUBLICATIONS

International Preliminary Report on Patentability, Date of Mailing: Jan. 17, 2013 for International Application No. PCT/US2011/042334 filed Jun. 29, 2011.

(Continued)

*Primary Examiner* — Thomas J Sweet
*Assistant Examiner* — Tiffany Shipmon
(74) *Attorney, Agent, or Firm* — Hamilton, Brook, Smith & Reynolds, P.C.

(57) ABSTRACT

An implant includes a collapsible anchor to be deployed within a lumen and a protrusion coupled to the anchor. The protrusion, in a constrained state, extends a distance from an exterior surface of the anchor and, in an unconstrained state, extends further from the exterior surface of the anchor. Also included is a biodegradable constraint, such as a biodegradable tube or suture, configured to maintain the protrusion in the constrained state until the constraint releases. The implant may include additional biodegradable constraints, each constraint configured to maintain the protrusion in a different constrained state and to degrade over a different predetermined period after the implant has been deployed within the lumen. The protrusion may include a bi-directional barb or an open loop. The protrusion may be configured to penetrate a wall of the lumen and to allow tissue to grow about the protrusion. The implant may also include an unsupported, thin-walled sleeve coupled to the anchor and configured to extend into the lumen upon deployment of the collapsible anchor.

30 Claims, 10 Drawing Sheets

(56) References Cited

U.S. PATENT DOCUMENTS

| | | | |
|---|---|---|---|
| 5,531,783 A | 7/1996 | Giele et al. | |
| 5,630,829 A | 5/1997 | Lauterjung | |
| 5,942,276 A | 8/1999 | Chivers et al. | |
| 6,558,429 B2 | 5/2003 | Taylor | |
| 6,558,492 B2 | 5/2003 | Goetz et al. | |
| 6,663,633 B1 | 12/2003 | Pierson | |
| 6,695,875 B2 | 2/2004 | Stelter et al. | |
| 6,730,056 B1 | 5/2004 | Ghaem et al. | |
| 7,025,791 B2 | 4/2006 | Levine et al. | |
| 7,081,132 B2* | 7/2006 | Cook et al. | 623/1.36 |
| 7,101,395 B2 | 9/2006 | Tremulis et al. | |
| 7,122,058 B2* | 10/2006 | Levine et al. | 623/23.65 |
| 7,160,312 B2 | 1/2007 | Saadat | |
| 7,267,694 B2 | 9/2007 | Levine et al. | |
| 7,329,285 B2 | 2/2008 | Levine et al. | |
| 7,338,520 B2 | 3/2008 | Bailey et al. | |
| 7,351,258 B2 | 4/2008 | Ricotta et al. | |
| 7,476,256 B2 | 1/2009 | Meade et al. | |
| 7,608,114 B2 | 10/2009 | Levine et al. | |
| 7,678,068 B2 | 3/2010 | Levine et al. | |
| 7,695,446 B2 | 4/2010 | Levine et al. | |
| 7,758,535 B2 | 7/2010 | Levine et al. | |
| 7,771,382 B2 | 8/2010 | Levine et al. | |
| 7,780,701 B1 | 8/2010 | Meridew et al. | |
| 7,815,589 B2 | 10/2010 | Meade et al. | |
| 7,819,836 B2 | 10/2010 | Levine et al. | |
| 7,837,643 B2 | 11/2010 | Levine et al. | |
| 7,914,568 B2 | 3/2011 | Cully et al. | |
| 8,029,455 B2 | 10/2011 | Stack et al. | |
| 8,057,420 B2 | 11/2011 | Meade et al. | |
| 8,137,301 B2 | 3/2012 | Levine et al. | |
| 8,162,871 B2 | 4/2012 | Levine et al. | |
| 2003/0144578 A1 | 7/2003 | Koster, Jr. | |
| 2004/0215324 A1 | 10/2004 | Vonderwalde et al. | |
| 2004/0220682 A1 | 11/2004 | Levine et al. | |
| 2005/0085923 A1 | 4/2005 | Levine et al. | |
| 2005/0102024 A1 | 5/2005 | Ricotta et al. | |
| 2005/0125020 A1 | 6/2005 | Meade et al. | |
| 2005/0143691 A1 | 6/2005 | Picha et al. | |
| 2005/0154448 A1 | 7/2005 | Cully et al. | |
| 2005/0240259 A1 | 10/2005 | Sisken et al. | |
| 2006/0009858 A1 | 1/2006 | Levine et al. | |
| 2006/0161139 A1 | 7/2006 | Levine et al. | |
| 2006/0212042 A1 | 9/2006 | Lamport et al. | |
| 2007/0083258 A1 | 4/2007 | Falotico et al. | |
| 2007/0270944 A1 | 11/2007 | Bergheim et al. | |
| 2008/0071383 A1 | 3/2008 | Levine et al. | |
| 2008/0097466 A1 | 4/2008 | Levine et al. | |
| 2008/0161922 A1 | 7/2008 | Rhoda | |
| 2008/0221673 A1 | 9/2008 | Bobo et al. | |
| 2008/0234834 A1* | 9/2008 | Meade et al. | 623/23.65 |
| 2009/0012541 A1 | 1/2009 | Dahl et al. | |
| 2009/0149871 A9 | 6/2009 | Kagan et al. | |
| 2009/0177215 A1 | 7/2009 | Stack et al. | |
| 2009/0182355 A1 | 7/2009 | Levine et al. | |
| 2009/0254174 A1 | 10/2009 | Case et al. | |
| 2009/0259306 A1* | 10/2009 | Rowe | 623/2.12 |
| 2009/0270966 A1* | 10/2009 | Douk et al. | 623/1.11 |
| 2009/0306763 A1 | 12/2009 | Roeder et al. | |
| 2010/0305590 A1 | 12/2010 | Holmes et al. | |
| 2011/0040318 A1 | 2/2011 | Marco et al. | |
| 2012/0179086 A1 | 7/2012 | Shank et al. | |

FOREIGN PATENT DOCUMENTS

| | | |
|---|---|---|
| JP | 2005-021504 | 1/2005 |
| WO | WO 99/49792 A1 | 10/1999 |
| WO | WO 00/18322 A1 | 4/2000 |
| WO | WO 03/024355 A1 | 3/2003 |
| WO | WO 03/057090 A1 | 7/2003 |
| WO | WO 2004/041133 A1 | 5/2004 |
| WO | WO 2004/087014 A2 | 10/2004 |
| WO | WO 2004/087233 A2 | 10/2004 |
| WO | WO 2006/002492 A1 | 1/2006 |
| WO | WO 2007/025028 A1 | 3/2007 |
| WO | WO 2007/038786 A1 | 4/2007 |
| WO | WO 2007/079413 A2 | 7/2007 |
| WO | WO 2007/136735 A2 | 11/2007 |
| WO | WO 2008/048973 A2 | 4/2008 |
| WO | WO 2009/029744 A1 | 3/2009 |
| WO | WO 2009/052188 A1 | 4/2009 |
| WO | WO 2009/085107 A1 | 7/2009 |
| WO | WO 2009/129079 A1 | 10/2009 |
| WO | WO 2010/126889 A1 | 11/2010 |
| WO | WO 2011/031981 A1 | 3/2011 |
| WO | WO 2012/006146 A1 | 1/2012 |

OTHER PUBLICATIONS

International Preliminary Report on Patentability mailed Mar. 22, 2012 for International Application No. PCT/US2010/048444 filed Sep. 10, 2010.

International Search Report and Written Opinion mailed Sep. 25, 2011 of International Application No. PCT/US2011/042334 filed Jun. 29, 2011.

International Search Report and the Written Opinion of the International Searching Autority, mailed Nov. 12, 2010 from PCT/US2010/048444 filed Sep. 10, 2010.

* cited by examiner

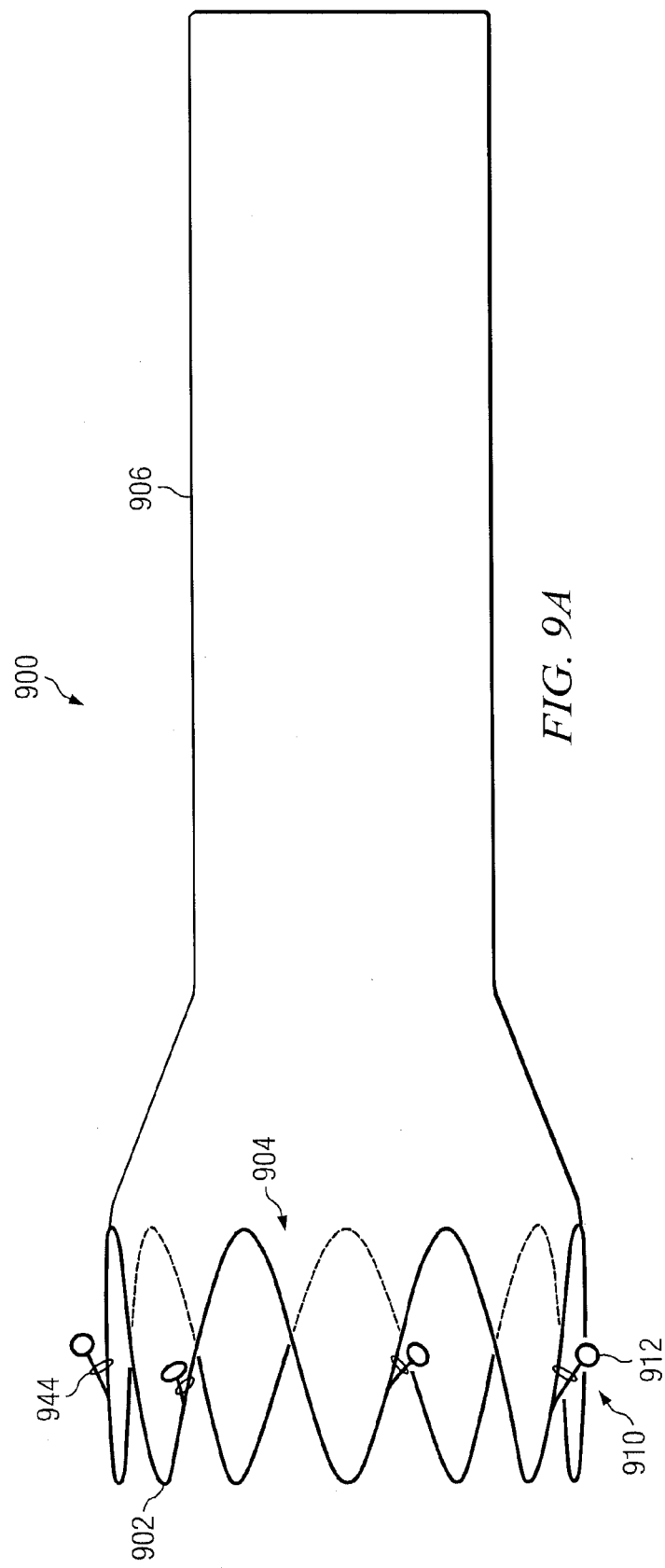

ANCHORS WITH BIODEGRADABLE CONSTRAINTS

RELATED APPLICATIONS

This application is a continuation-in-part of International Application No. PCT/US2010/048444, which designated the United States and was filed on Sep. 10, 2010, which claims the benefit of U.S. Provisional Application No. 61/276,381, filed on Sep. 11, 2009 and U.S. Provisional Application No. 61/361,806, filed on Jul. 6, 2010.

The entire teachings of the above applications are incorporated herein by reference.

BACKGROUND OF THE INVENTION

Obesity is associated with a wide variety of health problems, including Type 2 diabetes, hypertension, coronary artery disease, hypercholesteremia, sleep apnea, and pulmonary hypertension. It also exerts an enormous strain on the body that affects the organs, the nervous system, and the circulatory systems. Obesity rates have been rising for years in the United States, causing corresponding increases in healthcare expenditures.

Curing obesity has so far vexed the best efforts of medical science. Dieting is not an adequate long-term solution for most obese people, especially those with a body-mass index of over 30. Stomach stapling, or gastroplasty, reduces the size of the stomach, leading to reduced appetite and weight loss, but eventually the stomach stretches and the patient's appetite returns to pre-surgery levels. Roux-en-Y gastric bypass reduces the size of the stomach and the length of the intestine, and leads to both weight loss and alleviation of the Type 2 diabetes common to obese patients. Although gastric bypass appears to provide a more permanent solution than gastroplasty, complication rates associated with gastric bypass are between 2% and 6%, with mortality rates of about 0.5-1.5%.

Endoscopically delivered gastrointestinal implants, such as those described in commonly assigned U.S. Pat. Nos. 7,025,791 and 7,608,114 to Levine et al., incorporated herein by reference in their entireties, provide the benefits of gastric bypass without the hazards of surgery. For example, an implant may include a thin-walled, floppy sleeve that is secured in the stomach or intestine with a collapsible anchor. The sleeve extends into the intestine and channels partially digested food, or chyme, from the stomach through the intestine in a manner that may cause weight loss and improve diabetes symptoms. The sleeve and anchor can be removed endoscopically when treatment is over or if the patient desires.

SUMMARY OF THE INVENTION

Embodiments of the present invention provide improved anchoring of an implant in the gastrointestinal tract and can increase the duration that an implant can be anchored in the intestine by providing biodegradable constraints that maintain anchoring protrusions in a constrained state until the constraint releases.

An implant according to the principles of the invention includes a collapsible anchor to be deployed within a lumen and a protrusion coupled to the anchor. The protrusion, in a constrained state, extends between about 2 mm and about 4 mm from an exterior surface of the anchor and, in an unconstrained state, extends further from the exterior surface of the anchor. Also included is a biodegradable constraint, such as a biodegradable tube or suture, configured to maintain the protrusion in the constrained state until the constraint releases.

The biodegradable constraint typically covers at least a portion of the protrusion, such as the mid-portion, and may further cover a portion of the anchor. The implant may include additional biodegradable constraints, each constraint configured to maintain the protrusion in a different constrained state and to degrade over a different predetermined period after the implant has been deployed within the lumen. The protrusion may include a bi-directional barb, an open loop, and/or a helix and may be configured to penetrate a wall of the lumen. The protrusion can be coupled to the anchor between ends of the anchor. In an embodiment, the protrusion extends between about 4 mm and 8 mm from the exterior surface of the anchor when released from the constrained state.

A method of securing a collapsible anchor within a lumen includes deploying the collapsible anchor within the lumen, the collapsible anchor having a protrusion that, in a constrained state, extends between about 2 mm and about 4 mm from an exterior surface of the anchor. Further, the method includes maintaining the protrusion in the constrained state with a biodegradable constraint and penetrating a wall of the lumen with the protrusion in the constrained state to secure the anchor.

The method may include allowing tissue to grow about the protrusion. Further, the method may include allowing the biodegradable constraint to degrade over a predetermined period after the implant has been deployed in the lumen to release the protrusion from the constrained state. Further yet, the method may include bending the protrusion alongside the collapsible anchor to place the protrusion in the constrained state and inserting the protrusion, in the constrained state, into the lumen.

The collapsible anchor, which may, for example, be a wave anchor or a stent comprising a network of struts, is configured to be deployed within a lumen in a mammalian body. Upon deployment, the collapsible anchor expands within the lumen, and the protrusion, when released, expands away from the anchor, pushing the protrusion against the wall of the lumen. In some embodiments, the protrusion has a first end coupled to the anchor and a second end formed in an open loop. Over time, the protrusion and, if present, the open loop penetrate the luminal wall, and the protrusion and/or the open loop, may project through the far side of the luminal wall. A pocket of scar tissue forms about the open loop and through an opening in the open loop, securing the anchor within the lumen. The implant may have additional protrusions, each of which is connected to the anchor and can include an open loop. Each additional open loop also includes an opening and is adapted to penetrate the luminal wall upon deployment of the collapsible anchor.

Each open loop may have an inner opening with a width of between about 1 mm and about 13 mm, or, more preferably, an inner diameter of about 3 mm. Typically, the protrusion extends along a total length of between about 6 mm and about 13 mm from the collapsible anchor upon full deployment from the collapsible anchor. The protrusion and the open loop may be formed of wire (e.g., nitinol wire) with a preferred diameter of about 0.010 inch to about 0.040 inch, and more preferably about 0.020 inch.

The open loop can be formed of a loop of wire, and the protrusion can be formed of a straight length of wire extending from the loop of wire. The open loop may be oriented in a variety of directions with respect to the collapsible anchor. For example, the open loop may define a plane that is perpendicular to the lumen wall when the protrusion is deployed. Alternatively, the open loop may define a plane that is parallel to the lumen wall when the protrusion is deployed. When the protrusion is in a collapsed state, it folds against or along the side of the collapsible anchor. When relaxed or unconstrained, straight protrusions typically extend outwards from the collapsible anchor at an angle of between about 45 degrees and about 135 degrees, or, more preferably, to an angle of about 80 degrees or about 90 degrees. At these angles, the expanded straight protrusion pushes the loop outward, causing an edge of the loop to engage the luminal wall.

Alternatively, the protrusion can include a length of wire formed in a helix. The wire used to form the helix may be coiled to form the loop, which can be oriented such that it is parallel to the luminal wall when deployed within the lumen. (Other orientations of the loop are also possible.) The helix may have a tapered profile (e.g., a conical profile) when viewed from the side, and can be flattened alongside the collapsible anchor. The collapsed implant can be inserted into the lumen endoscopically. Releasing the helix and the anchor from the collapsed state causes the helix to push the loop away from the anchor, which, in turn, causes a face of the loop to engage the luminal wall. The implant may also include an end effect at or near the tip of the loop to aid penetration of the loop through the luminal wall.

The implant can be collapsed, for removal from the lumen, with an optional drawstring that runs through the opening in the loop or through additional retaining hooks or loops connected to the loop or the protrusion. Pulling on the drawstring collapses the loop and protrusion towards the collapsible anchor, and away from the luminal wall. Collapsing an implanted helix may cause coils in the helix to shear fibrotic tissue formed about the helix depending on the spacing and orientation of the coils that make up the helix.

An implant with a protrusion can also include an unsupported, thin-walled sleeve coupled to the collapsible anchor and configured to extend into the lumen (e.g., the intestine) upon deployment of the collapsible anchor. The implant may also include a restrictor plate instead of or in addition to the thin-walled sleeve.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 9A shows an implant that includes a sleeve extending from an anchor with open loop protrusions maintained in a constrained state by biodegradable constraints.

DETAILED DESCRIPTION OF EMBODIMENTS OF THE INVENTION

Figure 1A:
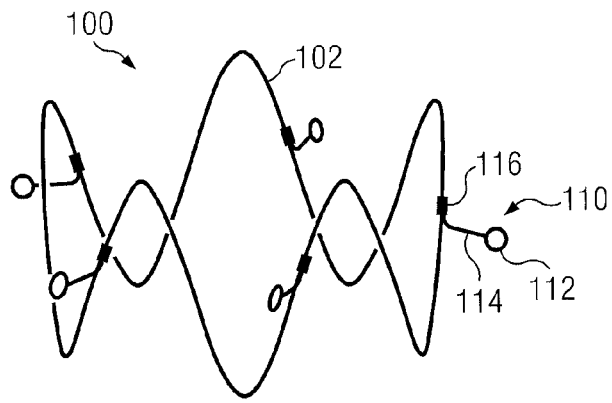
FIGS. 1A-1D are perspective, plan, and elevation views of straight protrusions with open loop s coupled to a wave anchor.

A description of example embodiments of the invention follows.

An anchor may be used to secure a sleeve in the intestine of a patient for treating obesity and/or type-2 diabetes as described in commonly assigned U.S. Pat. No. 7,025,791; U.S. Pat. No. 7,608,114; U.S. Pat. No. 7,476,256; U.S. Pat. No. 7,815,589; U.S. patent application Ser. No. 11/330,705, filed on Jan. 11, 2006, by Levine et al.; U.S. patent application Ser. No. 11/827,674 filed on Jul. 12, 2007, by Levine et al., all of which are incorporated herein by reference in their entireties.

As described in the above-referenced patents and patent applications, straight, sharp barbs fixed to a self-expanding anchor may be used to secure an implant to the duodenal wall. However, the body's healing response stimulates a progressive tissue proliferation around sharp barbs in response to the injury caused as the anchor pushes the sharp barbs into the wall of the duodenum. The inflammatory response to the injury produces a mix of granulation and more stable fibrous tissue (i.e., scar tissue). This causes thickening of the duodenal wall over time resulting in barbs disengaging from the tissue. Typically, the thickening of the duodenal wall is the result of infiltration of less stable, granulation tissue such that the tissue closest to the lumen is not very tough or stable. The thickening of the wall leads to the barbs disengaging from the muscle layer or the fibrotic scar tissue while still residing in the less stable, granulation tissue. As sharp barbs separate from the duodenal wall, the implant may become unstable and migrate or rotate within the duodenum.

Long barbs or protrusions tend to be better than short barbs or protrusions at holding implants securely for longer periods. Without subscribing to any particular theory, it appears that longer barbs or protrusions are more stable because it takes more time for the inflammatory thickening to separate longer barbs or protrusions from the muscle layer. However, there is a practical limit to how long sharp barbs can be because longer sharp barbs are more likely to infiltrate surrounding organs. Very long sharp barbs or long protrusions can pierce or erode through the muscle wall of the intestine and into adjacent structures and could potentially cause leaks, bleeding, or adhesions to other organs.

Protrusions with open loops (also called open heads), on the other hand, can secure an implant for longer periods of time while minimizing the risk of damage to nearby organs. In addition, protrusions or barbs can be deployed in a constrained state, e.g. having reduced barb height, to initially secure the anchor in the wall of the duodenum, and then released to an un-constrained state, e.g. having lengthened barb height, after a predetermined period of time to further improve anchoring stability. Deploying an implant having smaller barb heights can avoid complications with adjacent anatomy and facilitate packaging of the implant during endoscopic delivery. The ability to increase the barb height after implantation and in response to the natural healing mechanism of thickening of the duodenal wall allows for increased anchoring stability.

In one embodiment, the protrusion, which is relatively narrow (e.g., about 0.060 inch wide) and relatively long (e.g., about 13 mm long), connects a relatively broad open loop (e.g., about 3 mm in diameter) to a collapsible anchor. Upon deployment, the protrusion pushes the open loop against the intestinal wall. Without being bound by any particular theory, initial research suggests that the muscle layer in the intestine stretches across the loop, and it eventually thins out or erodes enough to allow the loop to penetrate the luminal wall. A chronic inflammation response causes scar tissue to form around the loop and through the opening formed by the loop; this scar tissue can hold the loop securely. Because the loop is rounded or otherwise shaped to promote erosion through the muscle wall, the protrusion and the loop are less likely to pierce the scar tissue or surrounding organs.

Straight Protrusions with Open Loops

Figure 1B:
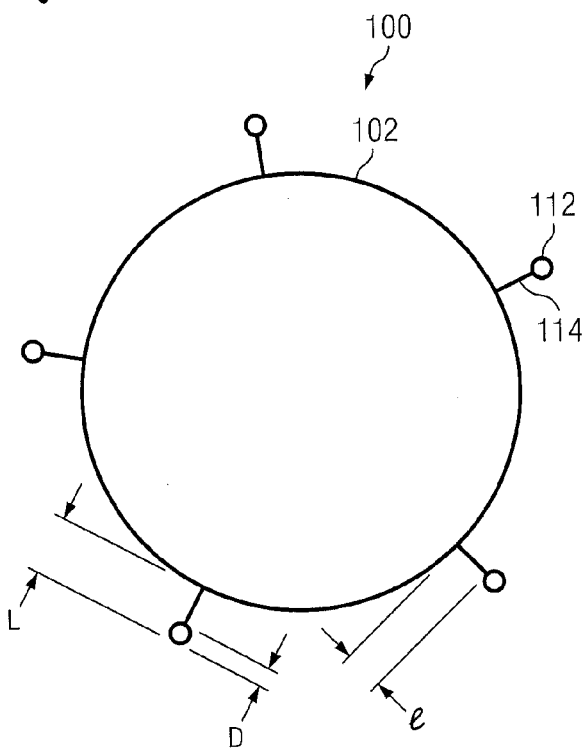
Figure 1C:
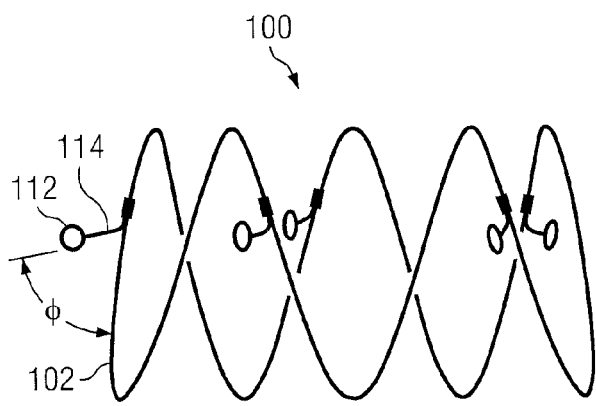
Figure 1D:
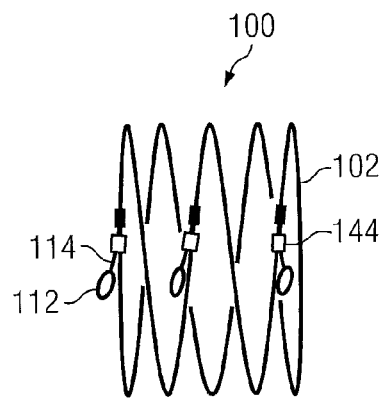

FIGS. 1A-1D show an implant 100 suitable for deployment within the gastrointestinal tract distal to the pylorus. The implant 100 includes a collapsible wave anchor 102 that includes a plurality of protrusions 110, each of which extends outward from the wave anchor 102. FIGS. 1A-1C show perspective, plan, and elevation views of the implant 100 in a relaxed state with protrusions 110 in an unconstrained state (from the top, the relaxed implant 100 looks circular); FIG. 1D is an elevation view of the implant 100 in a compressed state with protrusions 110 in a constrained state. As shown, protrusions 110 extend from the anchor 102 in the constrained state and extend further from the anchor in the un-constrained state. Typically, the implant 100 is compressed for endoscopic deployment within the gastrointestinal tract and inserted with the protrusions maintained in a constrained, or collapsed, state. Once positioned properly within the gastrointestinal tract, the implant 100 expands to the relaxed state shown in FIGS. 1A-1C. The protrusions 110, however, may be maintained in a constrained state, such as shown in FIG. 1D, until released after a predetermined period of time after the implant has been inserted in the gastrointestinal tract.

The anchor 102 may have a relaxed diameter of about 40 mm or greater, e.g., about 45 mm, about 50 mm, or about 55 mm. Each protrusion 110 includes a rounded loop 112 at the end of a narrow, straight neck 114, and each loop 112 includes an opening whose inner width D is within the range (inclusive) of between about 1 mm and about 13 mm, and preferably a diameter D within a range of about 1 mm and about 6 mm, or, more preferably, about 3 mm. The outer diameter can be within a range of about 2 mm to about 8 mm, and the diameter of the wire used to form each protrusion 110 can be within a range of about 0.010 inch to about 0.030 inch. Typically, the minimum bend radius of the wire limits the minimum inner diameter (it can be difficult to bend the wire too tightly), and the minimum desired pressure exerted by the loop 112 against the tissue limits the maximum inner diameter (bigger loops 112 may not exert enough pressure on the tissue to penetrate the tissue). The straight neck 114 has a length l of between about 6 mm and about 10 mm, for a total projection length L of between about 7 mm and about 13 mm. A crimp 116 or other suitable connection fixes the neck 114 to the wave anchor.

Each protrusion 110 folds down along the side of the wave anchor 102 when compressed for delivery. A biodegradable constraint 144, such as a biodegradable tube or suture, maintains the protrusions in a constraint state until the constraint releases. The protrusion, in a constrained state, may extend at least about 2 mm, e.g., between about 2 mm and about 4 mm, from an exterior surface of the anchor 102 and, in an unconstrained state, extend further from the exterior surface of the anchor. Each protrusion 110 may spring up to extend nearly perpendicularly from the wave anchor 102 when released from the compressed state to the relaxed or un-constrained state. Specifically, the angle $\phi$ formed by the protrusion 110 and a leg of the wave anchor 102 may be between about 45° and about 135°, or, more preferably, between about 75° and 105°, e.g., about 80° or about 90°.

For example, the biodegradable or erodible constraint 114 can be formed from PolyLactide (PLA), PolyGlycolic Acid (PGA), poly(lactic-co-glycolic acid) (PLGA), or any other material that degrades when implanted in the stomach or intestine. Materials used for sutures, such as silk, are suitable biodegradable materials for constraint 114. Another suitable material is polyethylene terephthalate (PET), which is commonly used for beverage containers and may degrade over a relatively long period of time after implantation. Different biodegradable materials differ in their degradation profile. For example, the duration over which a material degrades can range from hours to years and depends on multiple factors, including the environment to which the material is exposed. The degradation may occur according to a hydrolytic reaction, where water acts as a catalyst, or may occur in an acid based reaction.

Some biodegradable materials, such as PGLA, offer the advantage of also being bioresorbable (also referred to as bioabsorbable). In one example, a biodegradable constraint is a tube formed from PLGA, a bioresorbable polymer, which may be made using PLGA tubing available under the ZEUS® ABSORV PLGA brand. In another example, a biodegradable constraining element is formed using a bioresorbable suture. Advantageously, depending on the configuration of the biodegradable material, the constraint 114 can be formed to degrade after a predetermined period of implantation. At the predetermined period of time, preferably after the initial inflammatory response of the duodenal wall, the biodegradable constraint 114 dissolves allowing the protrusion to reach its full height, thereby providing additional stability in the duodenal wall.

In one example, an open loop protrusion 110 is formed of a single piece of nitinol wire with a diameter of about 0.020 inch. The wire is bent to form a pair of struts that can be crimped, bonded, or welded onto a single-wire leg of an anchor (e.g., wave anchor 102 in FIGS. 1A-1D) such that the single wire of the anchor leg nestles between the struts. The wire is bent to form the narrow, straight neck 114 and coiled twice to create the loop 112. The two loops of coil form a broad, blunt edge that can engage and erode the luminal wall such that the loop 112 eventually penetrates the luminal wall. Further details of the open loop protrusion are described in International Application No. PCT/US2010/048444, filed on Sep. 10, 2010, which is incorporated by references in its entirety.

Figure 2A:
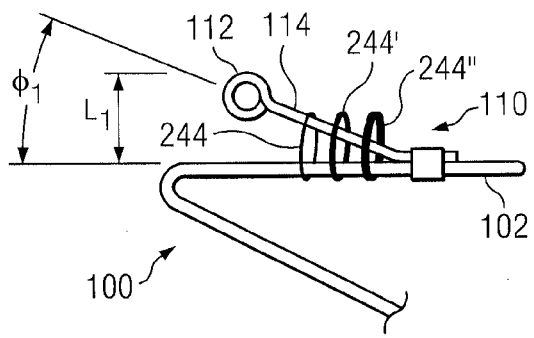
FIGS. 2A-2C illustrate how a straight protrusion with an open loop extends further from the anchor as biodegradable constraints release.
Figure 2B:
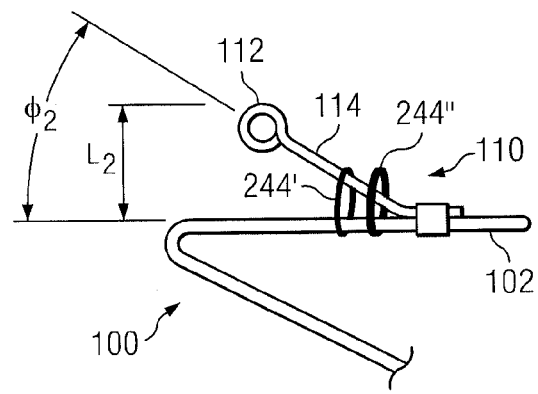
Figure 2C:
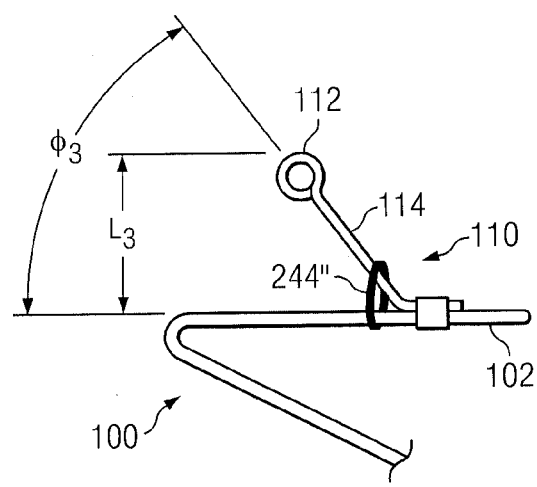

FIGS. 2A-2C illustrate how a straight protrusion 110 with an open loop 112 extends incrementally further from the anchor 102 as biodegradable constraints 244, 244', and 244" release. Each constraint is configured to maintain the protrusion in a different constrained state and to degrade over a different predetermined period after the implant has been deployed within the lumen. As shown in FIG. 2A, constraints 244, 244', and 244" wrap around neck 114 of protrusion 110 and around a strut of anchor 102. Each biodegradable constraint 244, 244', and 244" can be a suture that ties a portion of the protrusion 110 to a portion of the anchor 102, thereby maintaining protrusion 110 in respective constrained states. Different thicknesses of constraints 244, 244', and 244" are meant to illustrate that the constraints are configured to degrade at different periods of time. As shown, thin suture 244 is configured to degrade first, medium thickness suture 244' next, and thick suture 244" last. Alternatively or in addition, constraints or sutures 244, 244', and 244" may be formed from different biodegradable materials that differ in their respective degradation profiles.

FIG. 2A shows the implant 100 in a first constraint state with all constraints 244, 244', and 244" present. The implant 100 may for example be in this first constrained state immediately after deployment into the lumen. As shown, constraint 244 maintains protrusion 110 in the first constrained state such that protrusion 110 and a leg of the wave anchor 102 form angle $\phi_1$. The combination of the angle $\phi_1$ and the length of protrusion 110 results in protrusion 110 extending from the anchor 102 for a total projection length $L_1$. As shown, $L_1$ is measured from the surface of anchor 102 to loop 112 of protrusion 110. Constraints 244' and 244" may or may not cooperate with constraint 244 to maintain protrusion 110 in the first constrained state. As shown in FIG. 2A, constraints 244' and 244" form loose loops around neck 114 of protrusion 110 and anchor 102. In this example, the loose loops formed by constraints 244' and 244" do not constrain protrusion 110.

FIG. 2B shows the implant 100 in a second or intermediate constraint state after constraint 244 has degraded and implant 100 was released from the first constrained state. Only constraints 244' and 244" remain in the second constrained state. The implant 100 may for example be in this second constrained state after the luminal wall has responded to the implant with inflammatory tissue growth as described elsewhere herein. As shown, constraint 244' maintains protrusion 110 in the second constrained state such that protrusion 110 and a leg of the wave anchor 102 form angle $\phi_2$. The combination of the angle $\phi_2$ and the length of protrusion 110 results in protrusion 110 extending from the anchor 102 for a total projection length $L_2$. Preferably, angle $\phi_2$ is greater than angle $\phi_1$ and projection length $L_2$ is greater than projection length $L_1$. Constraint 244" may or may not cooperate with constraint 244' to maintain protrusion 110 in the second constrained state. As shown in FIG. 2B, constraint 244" is a suture that forms a loose loop around neck 114 of protrusion 110 and anchor 102. In this example, the loose loop of the suture does not constrain protrusion 110.

FIG. 2C shows the implant 100 in a third or final constraint state after constraint 244' has degraded and implant 100 was released from the first and second constrained states. Only constraint 244" now remains to keep protrusion 110 in the third constrained state. The implant 100 may for example be in this first constrained state immediately after deployment into the lumen. As shown, constraint 244' maintains protrusion 110 in the second constrained state such that protrusion 110 and a leg of the wave anchor 102 form angle $\phi_2$. The combination of the angle $\phi_3$ and the length of protrusion 110 results in protrusion 110 extending from the anchor 102 for a total projection length $L_3$. Preferably, angle $\phi_3$ is greater than angles $\phi_1$ and $\phi_2$ and projection length $L_3$ is greater than projection lengths $L_1$ and $L_2$.

Figure 3A:
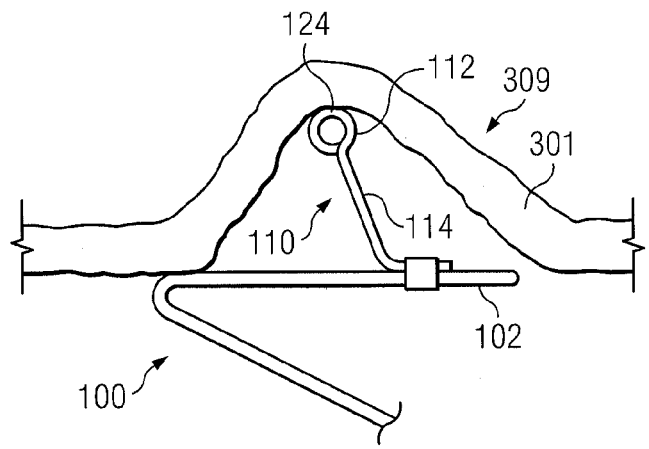
FIGS. 3A-3C illustrate how a straight protrusion with an open loop penetrates the wall of the gastrointestinal tract and how a fibrotic encapsulation forms about and through the open loop.
Figure 3B:
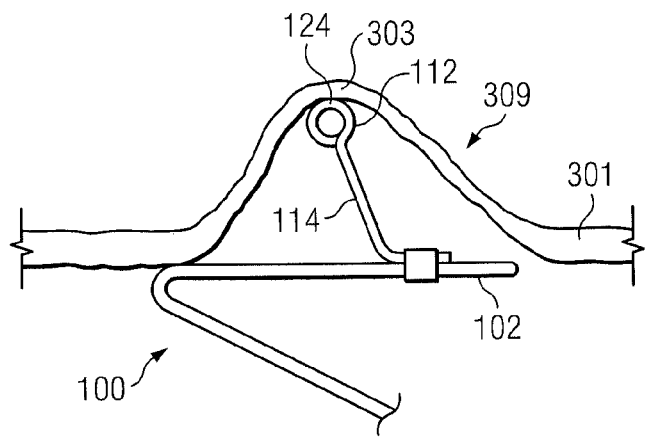
Figure 3C:
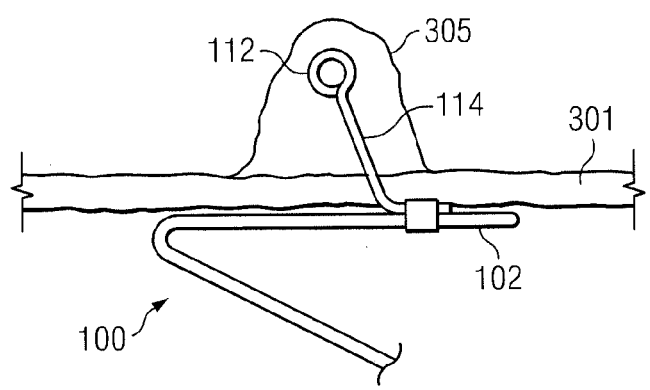

FIGS. 3A-3C illustrate how the implant 100 is secured within a lumen by a protrusion 110 with a relatively straight neck 114. First, the implant 100 is inserted into the lumen in a compressed state, with the projection 110 folded against the collapsed anchor 102. Once released into the lumen, the anchor 102 and the protrusion 110 expand toward their respective relaxed states, causing the edge 124 of the loop 112 to form a tent 309 in the luminal wall 301, which may include a muscle layer, as shown in FIG. 3A. Without being bound by a particular theory, initial studies suggest that, over time, the tent 309 stretches and the face 124 erodes at the point of contact 303, as shown in FIG. 3B. Eventually, the loop 112 erodes completely through the luminal wall 301, as shown in FIG. 3C. Within two to four weeks, fibrotic tissue 305 forms about and through the loop 112, securing the loop 112 with respect to the luminal wall 301, and may secure the loop 112 in a permanent or quasi-permanent fashion (e.g., for months or years). A loop 112 that is secured in a pocket of fibrotic tissue 112 does not appear to provoke the tissue remodeling that eventually forces other projections, such as sharp protrusions, out of the intestine.

Open-loop protrusions of different shapes are described in International Application No. PCT/US2010/048444, filed on Sep. 10, 2010, and incorporated by reference in its entirety. For example, a protrusion can be formed by bending wire into the shape of the Greek letter omega, Ω or by twisting wire into a loop. Protrusions may be separate pieces of wire bonded to an anchor or they may be formed of the same piece of wire that forms the anchor. An open-tip protrusion may include an erodible or biodegradable section that forms part of a loop connected to an anchor with a straight neck. The erodible section dissolves, turning the loop into an open prong that can be removed from tissue without tearing the tissue that forms in the opening of the loop due to the inflammatory response of the luminal wall. Typically, the erodible section is designed to dissolve during treatment, e.g., over six months, one year, two years, or possibly longer. A protrusion may include a corkscrew-like open head or a whisk-shaped head perched atop a straight neck coupled to an anchor 102. Tissue may grow about and through the openings between the windings in both the corkscrew-like head and the whisk-shaped head, just as in the helix protrusions described in greater detail below. Protrusion may also be bidirectional and can include a coil-like open head that engages the luminal wall as the protrusion expands from its constrained or collapsed state. The open heads may also be connected to the anchor with a detachable or erodible feature. For example, a coiled open loop can be connected to a straight neck with a bio-erodible or biodegradable element. Upon deployment, the loop erodes through the luminal wall and soon becomes encased in fibrotic tissue, securing the protrusion and attached anchor 102 in place. Over time, the bio-erodible element dissolves, causing the loop to become detached from the protrusion. Once the head is no longer connected to the protrusion, the protrusion can be withdrawn without necessarily tearing the scar tissue encapsulating the head, making for easier removal of the implant.

Helical Protrusions with Open Loops

Alternatively, the implant may include a helical protrusion instead of a straight protrusion. The helical protrusion acts as a coil spring that pushes the open loop into the lumen wall, but in a manner that distributes the load from the collapsible anchor to the contacting tissue over a longer length as compared to a straight protrusion of similar height. Upon initial engagement with the duodenal wall, the helix, if so designed, compresses. As the tissue and helix protrusion come to equilibrium the helix approaches full expansion, causing the loop to penetrate the luminal wall. Eventually, fibrotic tissue encapsulates the loop and the expanded helix, creating a pocket that holds the loop and helix securely. Like straight protrusions with open loops, helical protrusions with open heads may be designed for permanent, quasi-permanent, or temporary implantation. Furthermore, the helical protrusion can be inserted into the lumen in a constrained state. A biodegradable constraint, such as a biodegradable suture, can maintain the helical protrusion in the constrained state until the constraint releases.

Figure 4A:
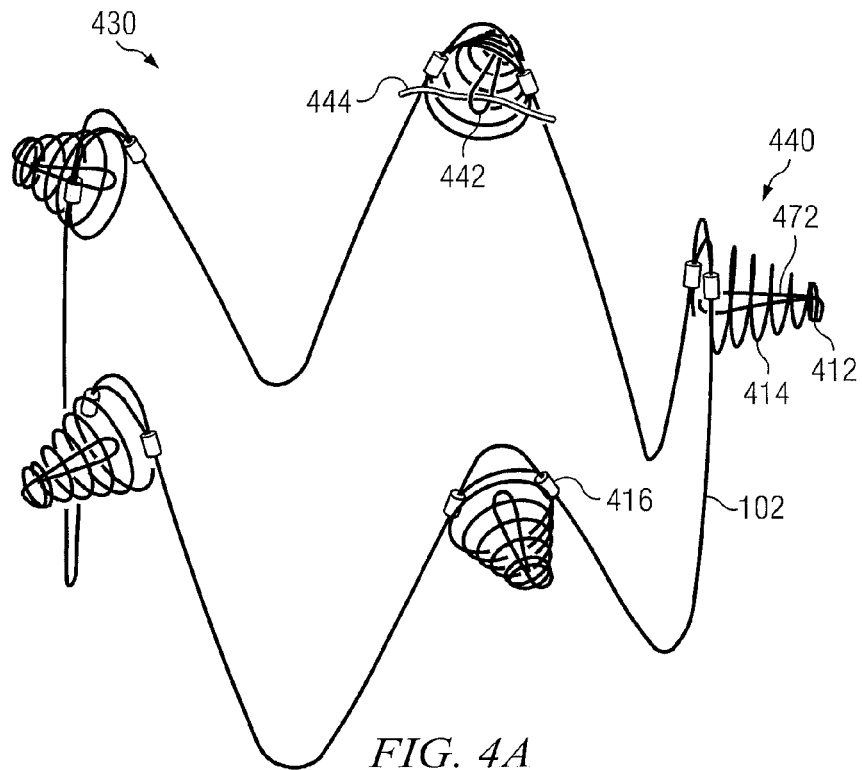
FIGS. 4A-4B are perspective views of wave anchors with helical protrusions with open loops.
Figure 4B:
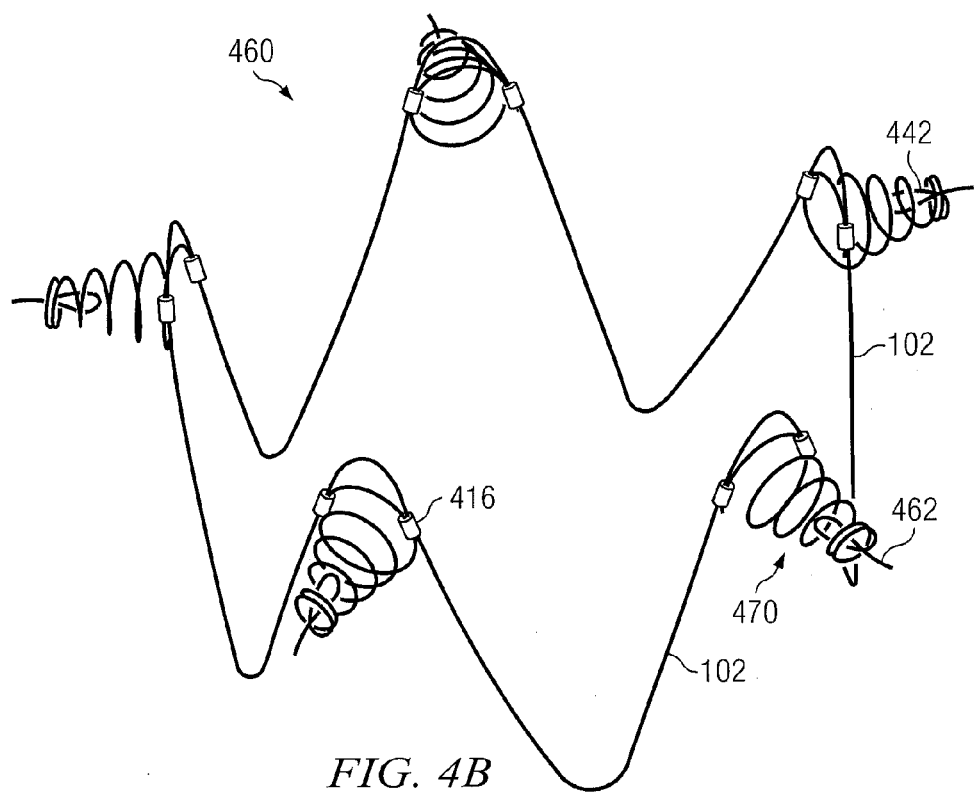

FIGS. 4A-4B are perspective views of implants that include projections with helical protrusion: FIG. 4A shows shows helical protrusions with retaining loops; FIG. 4B shows helical protrusions that include retaining loops and short end effects that promote initial penetration of the open loop into the muscle wall. FIG. 4A shows an implant 430 that includes five helical protrusions 440, each of which is coupled to a wave anchor 102 with a respective crimp 416. (Alternatively, the protrusions 440 may sutured or releasably coupled to the anchor 102.) Each helical protrusion 440 includes a helix 414 formed of several wire coils and a loop 412 formed of two loops of wire. The opening of each head 412 is parallel to the lumen defined by the wave anchor 102. Each helical protrusion 440 has a tapered profile, with the top coils (i.e., those farthest away from the wave anchor 102) being substantially smaller than the base coils (i.e., those closest to the wave anchor 102). Each coil in the helix 414 limits the penetration of the coil above it.

The top coils are sized to focus the force from the expanding implant 430 to penetrate the duodenal wall and to ultimately elicit the healing response. Top coils approximately 3 mm in diameter are small enough to start to burrow through the muscle layer. The base coils are larger than the top coils and are sized to substantially match and blend to the crowns (vertices) of the wave anchor 102. For example, a 7 mm diameter base coil blends well to the wave anchor 102 approximately 6 mm below the crowns, but larger base coils could be used for other attachment configurations and/or anchor configurations. Typically, the outer diameter of the largest coil in the helix 414 is within the range of about 1.5 mm to about 12 mm, and the coils have an inner diameter that ranges from about 1.0 mm to about 10 mm The loop 412 can have an inner diameter within a range of about 1.0 mm and about 6.0 mm.

The spacing of the coils or wire wraps in the helix 414 influences the tissue response. If the coils are too close together, then tissue may not be able to grow around the wire or between the coils. If the coils are too far apart, then each coil may exert more localized force on the tissue, causing the tissue to erode at the point of contact. In addition, increasing the coil spacing makes it more likely that the upper coils will infiltrate surrounding organs. Setting the spacing between wraps, or coil pitch, within a range of about 1.0 mm to about 4.0 mm (or, more preferably, within a range of about 2.4 mm to about 2.5 mm), limits the erosion caused by the upper coils while allowing for tissue encapsulation of helix 414.

In the examples shown in FIGS. 4A-4B, the loop 412 is formed of two coils of uniform diameter that are stacked upon each other, approximating a solid cylinder that does not compress. Because the loop 412 is relatively incompressible, it erodes through the duodenal wall, but only to an extent determined by the length and compliance of the helix 414. A helix 414 with appropriate compliance typically prevents the loop 412 from penetrating much beyond the muscle layer of the duodenal wall.

FIG. 4A shows implant 430 with several projections 440, each of which includes a retrieval element 442 that extends from the loop 412 towards the wave anchor 102. In the example shown in FIG. 4A, the retrieval element 442 is a loop of wire formed with an optional hypodermic tube 472, which provides an additional surface for fibrotic tissue to encapsulate; this further encapsulation may increase the anchoring strength. Each retrieval element 442 fits in the conical cavity defined by its associated helical neck 414 and can be used to exert a force normal to the axis of the conical cavity on the helical protrusion 410. For example, a normal force can be used to prevent or slow expansion of the helical protrusion 410 or to collapse an expanded helical protrusion 440. Other retrieval elements may be hooks, balls, or other suitable features for applying a normal force to the helix.

In the example shown in FIG. 4A, a constraint 444 threaded through the retrieval element 442 keeps the helical protrusion 440 in a fully or partially collapsed state. In some cases, the constraint 444 is a suture or biodegradable element that allows the user to influence how quickly the helical protrusion 440 expands after implantation, which, in turn, affects how quickly the loop 412 penetrates the luminal wall. Releasing tension on the suture or engineering the decay time of the biodegradable element allows the helix 414 to open to its full height more slowly, prolonging the equilibrium time and slowing the effect of the helical protrusion 440 on the contacting tissue.

A drawstring (not shown) that runs through some or all of retrieval elements 442 can be used to withdraw the protrusions 440 from the luminal wall. Pulling on the drawstring applies a normal force directly to the loops 412, causing the loops 412 to collapse into the coils below to disengage the helix 414 from the surrounding tissue. As the coils collapse, one within the next, they act as a "cheese cutter": each coil helps to shear the surrounding tissue from the coil above it as the above coil passes through the lower coil, freeing the helical protrusion 440 from any scar tissue that may have grown through or around the wire in the loop 412 and the helix 414. Pulling on the drawstring also causes the anchor 102 to collapse for endoscopic withdrawal from the implantation site as described below.

FIG. 4B shows an implant 460 with an end effect 462 at the end of each helical protrusion 470. In this example, each end effect 462 is a post that is oriented in the center of a respective helical protrusion 470 and protrudes slightly beyond the loop 412 of the respective helical protrusion 470. The end effects 462, which may be sharpened to engage the contacting tissue more quickly, initiate an injury to the duodenal wall and lead the heads 412 through the duodenal wall. Because each end effect 462 pierces the luminal wall, it initiates the injury that causes fibrotic tissue to encapsulate its associated helical protrusion 470 more quickly. Quickly embedding the helical protrusion 470 is important for stabilizing and maintaining placement of the implant in a mobile vessel with pressurized luminal contents, such as the duodenum or other portion of the intestines.

Implant 430 may also include a constraint 444 (not shown in FIG. 4B) threaded through the retrieval element 442 keeps the helical protrusion 470 in a fully or partially collapsed state. As described above, the constraint 444 can be a suture or biodegradable element that allows the user to influence how quickly the helical protrusion 440 expands after implantation, which, in turn, affects how quickly the loop 412 penetrates the luminal wall.

Figure 5:
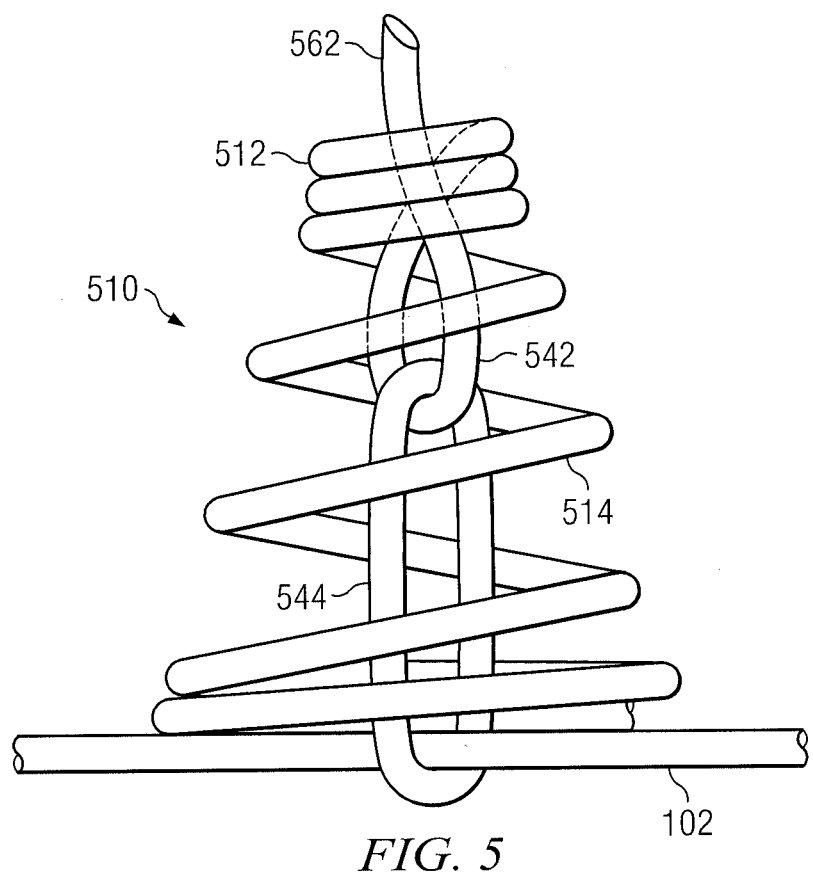
FIG. 5 is a perspective view of a loop projection with a helical neck and a biodegradable restraint.

FIG. 5 is a perspective view of an alternative helical protrusion 510 with a retrieval element 542 formed of a single wire without a hypodermic tube. The wire is coiled to form a helix 514 and a loop 512, then folded and formed into a retrieval element 542. Excess wire extending from the tail of the retrieval element 542 is trimmed and may be sharpened to create an end effect 562. The base coil of the helix 414 can be trimmed and/or bent as necessary before the projection is attached to the wave anchor 102, e.g., with a crimp 416, as shown in FIGS. 4A-4B, or using any other suitable attachment. Alternatively, the helical protrusion can be fabricated with a post that runs up its center, and the post can be crimped or otherwise affixed to the anchor 102. A constraint 544 threaded through the retrieval element 542 can keep the helical protrusion 510 in a fully or partially collapsed state. As shown, constraint 544 is a suture that ties retrieval element 542 to a strut of anchor 102. The constraint 544 can be a biodegradable suture that allows the user to influence how quickly the helical protrusion 510 expands after implantation, which, in turn, affects how quickly the loop 512 and end effect 562 penetrate the luminal wall.

Figure 6A:
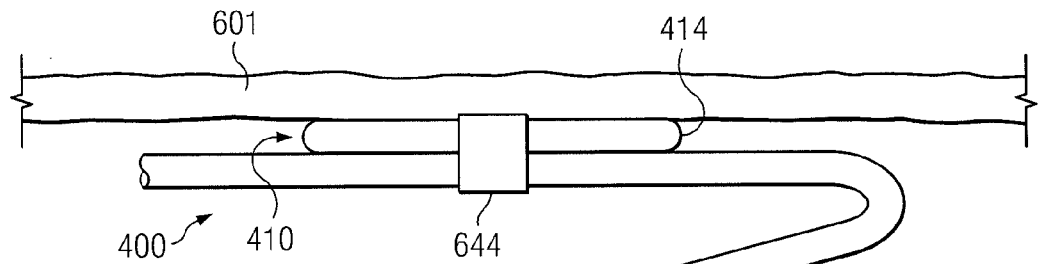
FIGS. 6A-6C illustrate how a helical protrusion with an open loop extends upon release of a biodegradable restraint and penetrates the wall of the gastrointestinal tract.
Figure 6B:
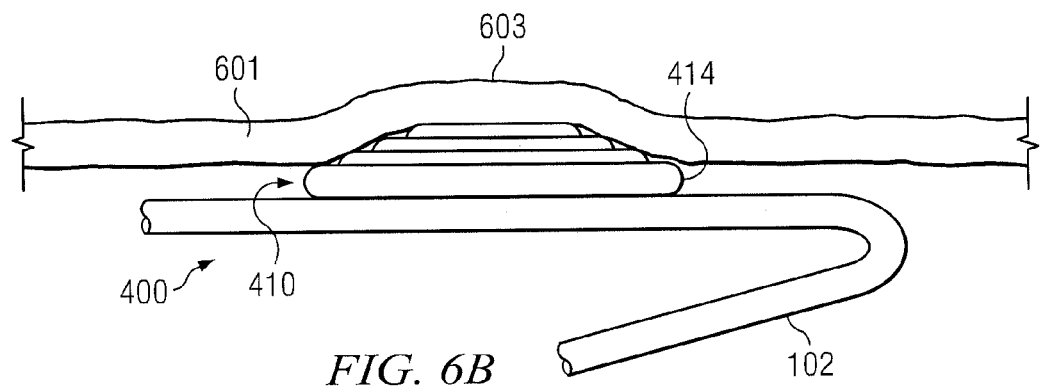
Figure 6C:
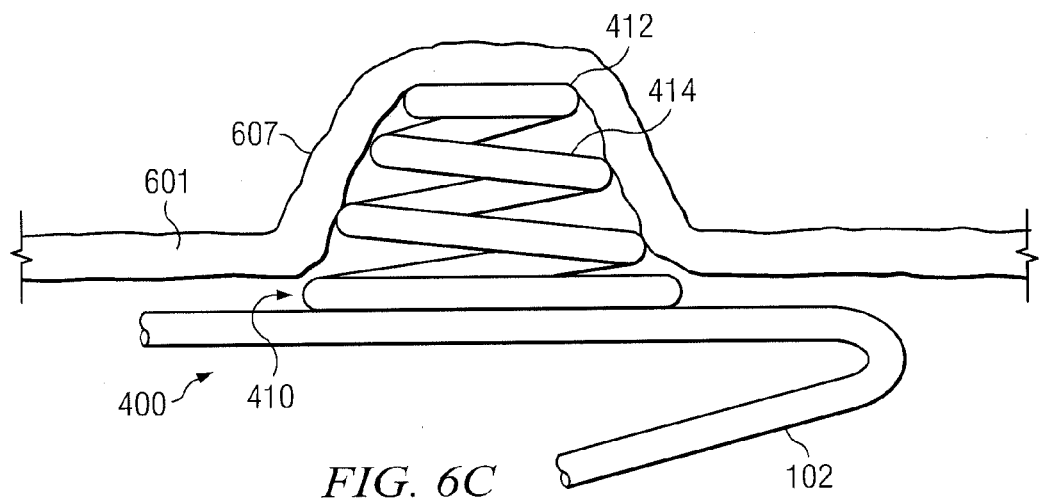

FIGS. 6A-6C show how a helical protrusion 410 engages a luminal wall to secure an implant 400 within the lumen. Helical protrusion 410 is similar to helical protrusion 440 shown in FIG. 4A and, like protrusion 440, may optionally include retrieval element 442 (not shown in FIG. 6A). The implant 400 is inserted into the lumen in a compressed or constrained state, with the helical protrusion 410 collapsed against the collapsed anchor 102, as shown in FIG. 6A. A biodegradable constraint 644 is configured to maintain the protrusion in the constrained state until the constraint 644 releases. Although FIG. 6A shows protrusion 410 collapsed flat against anchor 102, protrusion 410 can extend from anchor 102 in the constrained state. In addition, protrusion 410 can include an end effect that extends from the anchor, such as end effect 562 shown in FIG. 5.

Releasing the helical neck 414 allows the helical neck 414 to expand, causing a tent 603 to form in the duodenal wall 601, as shown in FIG. 6B. As the neck 414 continues to expand against the duodenal wall 601, it pushes the loop 412 through wall 601, as shown in FIG. 6C. Scar tissue 607 forms about and possibly through the loop 412 and neck 414. Without being bound by any particular theory, initial studies suggest that helical necks 414 tend to encourage more fibrotic encapsulation than straight necks of similar height because helical necks have more wire in contact with the tissue.

The compliance of the helical neck 414 affects how quickly the loop 412 penetrates the luminal wall 601. Initial studies suggest that the top-most coils in the helical neck 414 continue to push through tissue after initial contact until the contacting tissue and helix 414 come to equilibrium. If the helical neck 414 is as compliant as the luminal wall, however, then the neck 414 will not be able to push the loop 412 through the luminal wall 601. Since the compliance of the helical neck 414 is largely a function of wire diameter and pitch, increasing either the wire diameter or the pitch the wire diameter generally increases the rigidity of helical neck 414. Increasing the wire diameter too much may make it difficult to form the wire into tight loops to shape the loop 412. Wire with a diameter in the range of about 0.016 inch to about 0.040 inch is generally suitable for helical protrusions 410. Nitinol wire with a diameter of about 0.019" offers a balance: it can be formed into tight bends for the end of the helical neck 414 and the loop 412, yet forms a helix that is stiffer than the luminal wall 601. It can also be packed into a capsule for endoscopic delivery. The diameter of the helix 414 can also be varied to further customize the transition in stiffness and tissue response.

Although FIGS. 4-6 show a helix 414 with a linear transition between successive coil diameters, alternative helixes can have other shapes, including parabolic profiles, cylindrical profiles, hourglass profiles, and conical profiles (e.g., with the vertex of the cone connected to the anchor). Alternatively, the helix 414 can be formed in a flattened coil that is narrow at the center and flares out from the center into a flat spiral shape. The helix 414 could also be formed of a post that terminates in a coil with its wrappings aligned or angled with respect to one another in a corkscrew-like fashion. Compared to other three-dimensional shapes, tapered shapes tend to be easier to disengage from a mating surface. Parabolic shapes transition more quickly from large coils to small coils, facilitating a lower profile protrusion. Similarly, transitions between coils or wraps in the helix 414 can be customized as desired. For example, the coils in the helix 414 can be sized such that each coil fits into the coil below. This sizing of successive coils facilitates a lower profile for packing into the delivery catheter and facilitates disengagement from the duodenal wall.

Compliance Measurements

The compliance/stiffness of the protrusions disclosed herein can be characterized, in part, by the force required to deflect the protrusions from their respective relaxed (extended) states towards their respective collapsed states. For a protrusion with a straight neck (e.g., protrusion 110 of FIGS. 2A-2C), compliance may be defined, in part, by the normal force required to deflect the protrusion at room temperature by a given amount towards the strut of the collapsible anchor. Measurement shows that applying a force of at least about 0.1 lbf normal to the head (i.e., parallel to the long axis of the lumen) completely collapses a straight-necked protrusion made of 0.010-inch diameter nitinol wire, with a total length of 13 mm, ending in a loop formed of two wraps of wire with an inner diameter of about 3 mm. Similar measurement shows that applying about 0.8 lbf normal to the head deflects the head by about 0.250 inch for a straight-necked protrusion made of 0.020-inch diameter nitinol wire, with a total length of 11.5 mm, ending in a loop formed of two wraps of wire with an inner diameter of about 3 mm. Other straight-necked protrusions may be deflected by about 0.250 inch from their relaxed positions by forces within a range of about 0.80 lbf to about 0.95 lbf.

The compliance of a helical protrusion can be characterized, in part, by measuring the force required to (partially) collapse the helical protrusion at room temperature. Measurement shows that applying a force normal to the long axis of a helical protrusion within a range of about 0.19 lbf to about 1.75 lbf, or, more preferably, about 0.32 lbf to about 0.95 lbf, collapses the protrusion by about 0.250 inch, depending on the wire diameter, coil pitch, and coil size:

TABLE 1

Normal force applied to compress nitinol helical protrusions by 0.250 inch at room temperature

| Protrusion Height | Base Coil Diameter | Top Coil Diameter | Coil Spacing | Wire Diameter | Normal Force |
|---|---|---|---|---|---|
| 10 mm | 6 mm | 3 mm | 2.4 mm | 0.016" | 0.19 lbf |
| 6 mm | 6 mm | 3 mm | 4.0 mm | 0.023" | 0.32 lbf |
| 10 mm | 6 mm | 3 mm | 2.4 mm | 0.028" | 0.95 lbf |
| 10 mm | 6 mm | 3 mm | 2.4 mm | 0.030" | 1.75 lbf |

In addition to the compliance of the helix as measured in the normal force to compress the helix, resistance to bending must be considered. Helix stiffness can also be characterized by the force required to deflect the helix sideways, i.e., in the plane normal to the long axis of the helix. A balance must be struck between compressability and rigidity. Deflecting a nitinol helical protrusion with a 6 mm height, 6 mm base coil diameter, 3 mm top coil diameter, 4.0 mm coil spacing, and 0.020-inch wire diameter sideways by 0.250 inch at room temperature takes a force of at least about 0.033 lbf. Increasing the wire diameter to about 0.028 inch increases the force to about 0.135 lbf for a 0.250-inch deflection at room temperature. A preferred balance can be defined within the specifications above.

Bidirectional and Compound Barbs

Figure 7A:
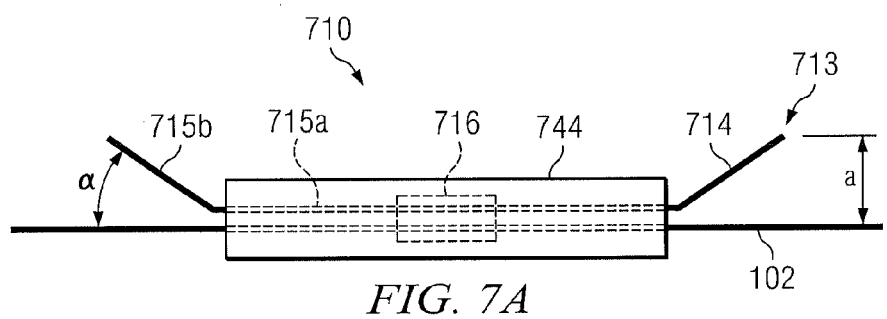
FIGS. 7A-7D show compound barb protrusions in un-constrained and constrained states.
Figure 7B:
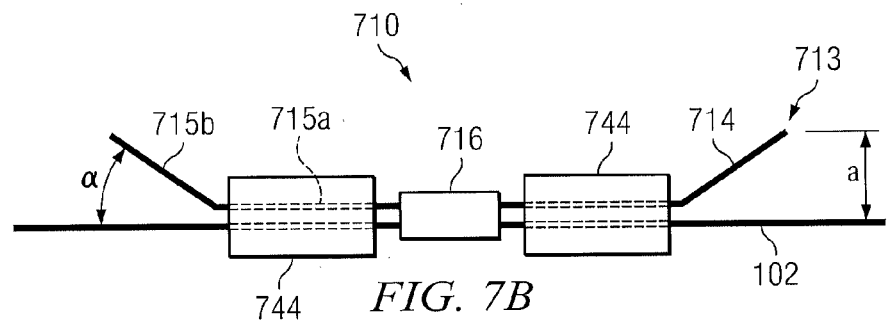
Figure 7C:
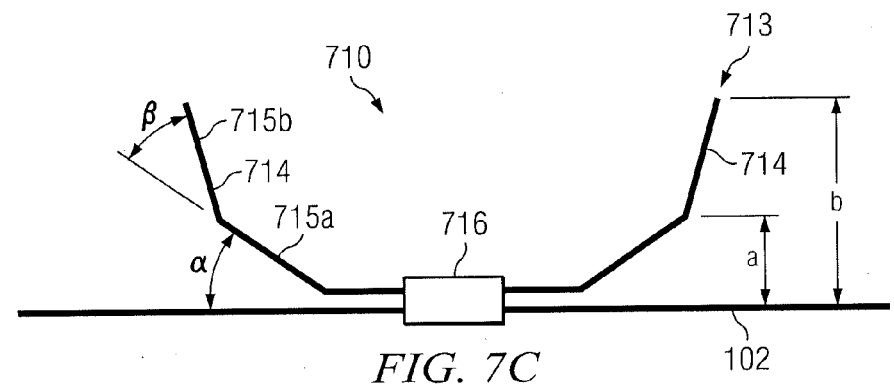
Figure 7D:
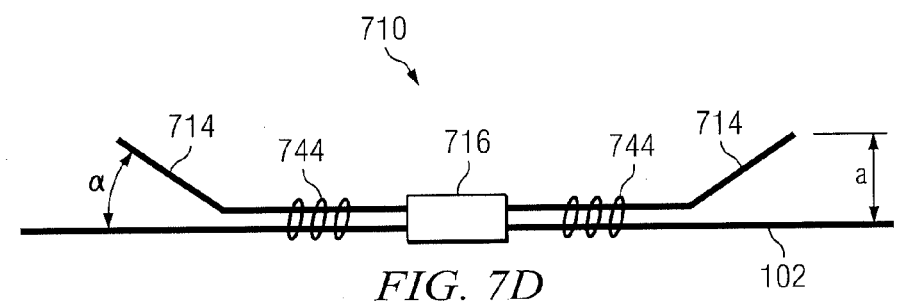

FIGS. 7A, 7B and 7D show compound barb protrusions 710 in constrained states, the protrusions 710 being maintained in the constrained states by respective biodegradable constraints 744. FIG. 7C shows a compound barb protrusion 710 in an un-constrained state, for example after the release of the constraint 744.

FIG. 7A shows protrusion 710 coupled to anchor 102 in a constrained state extending from the exterior surface of the anchor to a height a. Preferably, the height a to which the protrusion extends from anchor 102 is at least about 2 mm, e.g., between about 2 mm and about 4 mm. The projection height a is measured from an exterior surface of the anchor to the tip or end 713 of a leg 114 of protrusion 710. In an unconstrained state, protrusion 710 extends further from the exterior surface of the anchor, as described with reference to FIG. 7C below.

As shown in FIG. 7A, protrusion 710 is a bidirectional barb that includes two tines or legs 714 with ends directed in opposite directions from each other and outwardly from the anchor 102, of which one tine is so oriented at an oblique angle as to prevent longitudinal movement of the implant in a first direction and another tine is so oriented at an oblique angle as to prevent longitudinal movement of the implant in a second direction substantially opposite to the first direction. As shown, the oblique angles of the two legs 714 may be the same angle α. The angle α and the length of leg 714 determine the projection height a. In a constrained state, a portion of protrusion 710, e.g. segment 715b of leg 714, may extend outward from the anchor 102 at an angle α of between about 30 degrees to about 50 degrees, preferably at about 41 degrees. The barb protrusion 710 may include a sharp point at the end 713 of leg 714 to pierce tissue and provoke an inflammatory response.

A biodegradable constraint 744 is configured to maintain the protrusion in the constrained state until the constraint releases. Biodegradable constraint 744 can be made from any suitable biodegradable material as described herein. Constraint 744 can cover a portion of protrusion 710 and may also cover a portion of anchor 102. In one embodiment, constraint 744 is a bioresorbable tube formed from PLGA that covers a mid-portion of protrusion 710 and a strut of anchor 102. The PLGA tube maintains the protrusion 710 in a constrained state, extending from the anchor 102 at a height a, until the tube dissolves. Height a may be at least about 2 mm, or between about 2 mm and 4 mm.

Preferably, protrusion 710 is a bidirectional barb constructed of a shape memory alloy (e.g., Nitinol or similar) with a compound angle shape set into the barb. A releasable restraining mechanism, such as biodegradable constraint 744, allows the compound barb to change height over a predetermined period of time in the body. The compound shape of the barb protrusion is best described with reference to FIG. 7C.

As shown in FIG. 7C, the protrusion 710 includes a first segment 715a proximate the anchor 102 that extends from the anchor 102 along a first axis. The first segment 715a and anchor 102 form an angle α, the end of the first segment that is distal to the anchor being at a height a from the exterior surface of the anchor. Protrusion 710 also includes a second segment 715b that extends from the first segment 715a along a second axis oriented at an oblique angle β to the first axis. The combination of the lengths of the segments 715a and 715b and the angles α and β result in the protrusion to extend from the surface of anchor 102 at a height b. In one example, protrusion 710 extends to a height b of between about 4 mm and about 8 mm when released from the constrained state. In an un-constrained or relaxed state, a portion of protrusion 710, e.g. segment 715a, may extend outward from the anchor 102 at a combined angle of between about 41 degrees and about 90 degrees, preferably at an angle of about 82 degrees.

In the constrained state shown in FIG. 7A, the first axis is aligned with surface of the anchor 102 and first segment 715a is collapsed against anchor 102. In the constraint state, the first segment 715a of protrusion 710 may be covered in whole or in part by biodegradable constraint 744. In the example shown in FIG. 7A, the protrusion 710 is a bidirectional barb having two legs 714 of equal length that are formed symmetrically bout a mid-point of the protrusion. At the mid-point, the protrusion is connected to anchor 102 with crimp 716 or other suitable connection. Biodegradable constraint 744 covers crimp 716 and segments 715a of symmetrically formed legs 714. The legs 714, however, need not be of equal length or symmetrically formed, nor need the biodegradable constraint 744 cover the midpoint of the protrusion 710 or cover the protrusion 710 in a symmetric configuration. In some embodiments, multiple constraints are used to keep the protrusion in a constrained state.

FIG. 7B shows protrusion 710 as in FIG. 7A, except that two constraints 744 are used to separately tie the two legs 714 of protrusion 710 to anchor 102. Each of the constraints 744 holds one leg 714 of the protrusion 710 in a constrained state. The two constraints 744 may be engineered to degrade at about the same of a different period of time after the protrusion has been implanted in the lumen. As shown in FIG. 7B, constraints 744 can be tubes, for example formed from PLGA polymer, that wrap around legs 714 and anchor 102.

FIG. 7D shows protrusion 710 as in FIG. 7A, except that two sets of constraints 744 are used to separately fix the two legs 714 of protrusion 710 to anchor 102. Each of the constraints 744 holds one leg 714 of the protrusion 710 in a constrained state. The two sets of constraints 744 may for example be bioresorbable sutures that can be engineered to degrade at about the same of a different period of time after implantation. For example, by configuring individual sutures to degrade at different times, a user can control the incremental release of protrusion 710 from the initial constrained state shown in FIG. 7D. In his way, the protrusion 710 can be inserted into the lumen in an initial constrained state and at an initial height a, and thereafter allowed to incrementally extend further from anchor 102 as the constraints 744 incrementally release.

Figure 8A:
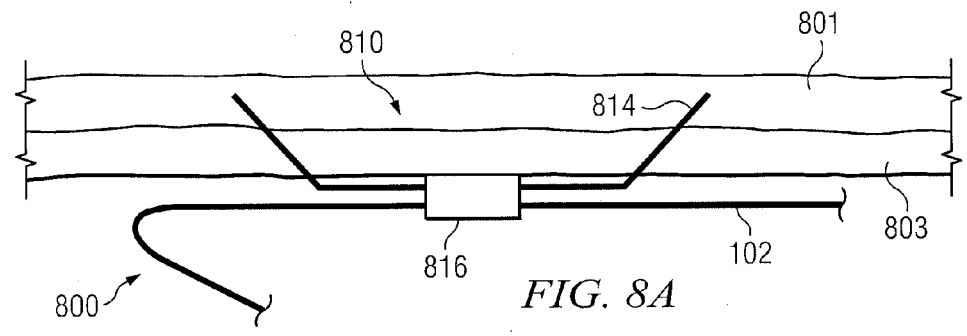
FIGS. 8A-8B illustrate how the tissue responds to a conventional barb penetrating the wall of the gastrointestinal tract.
Figure 8B:
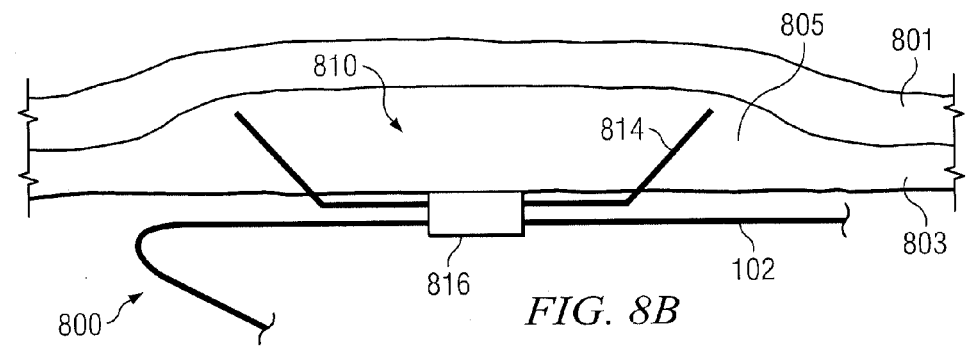

FIGS. 8A-8B illustrate how the tissue responds to an implant 800 having a conventional barb 810 penetrating the wall of the gastrointestinal tract. FIG. 8A shows implant 800 having barb 810 engaging the luminal wall 801, 803 in an initial conditional after deployment into the lumen. Barb 810 is coupled to anchor 102 of implant 800 with crimp 816. Barb 810 has tines 814 that have pierced the mucosa 803 and the muscle layer 801 of the luminal wall. The mucosa 803 is relatively soft tissue, while the muscle layer 801 is relatively tough tissue. FIG. 8B shows implant 800 after tissue remodeling has taken place over a period of time after implantation. As described above, the body's healing response stimulates a progressive tissue proliferation around the barb 810 in response to the injury caused as the anchor 102 pushes the tines 814 of barb 810 into the wall of the duodenum. The inflammatory response to the injury causes thickening of the duodenal wall over time resulting in the tines 814 of barb 810 disengaging from the tissue. Typically, the thickening of the duodenal wall is the result of infiltration of less stable, granulation tissue 805, such that the tissue closest to the lumen is not very tough or stable. Tougher tissues, such as the muscle layer 801 and the scar tissue that forms around the barb ends, remodel at a distance. The thickening of the wall leads to the barb 810 disengaging from the muscle layer 801 or the fibrotic scar tissue while still residing in the less stable, granulation tissue 805 and mucosa 803. As barb 810 separates from the duodenal wall, the implant 800 may become unstable and migrate or rotate within the duodenum.

Figure 8C:
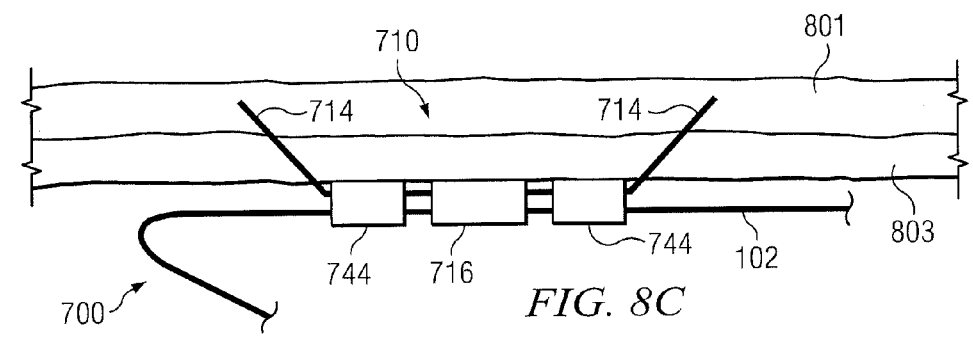
FIGS. 8C-8D illustrate how tissue responds to a compound barb penetrating the wall of the gastrointestinal tract and further extending upon release of a biodegradable restraint.
Figure 8D:
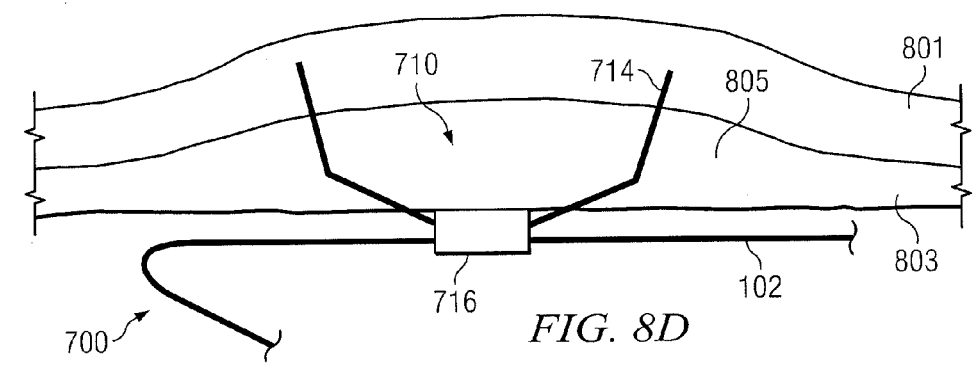

FIGS. 8C-8D illustrate how tissue responds to an implant 700 having a compound barb 710 penetrating the wall of the gastrointestinal tract and further extending upon release of a biodegradable restraints 744. FIG. 8C shows implant 700 having protrusion 710 engaging the luminal wall 801, 803 in an initial conditional after deployment into the lumen. Protrusion 710 is a compound barb protrusion as described above with reference to FIGS. 7A-C. Protrusion 710 is coupled to anchor 102 of implant 700 with crimp 716. As shown in FIG. 8C, two biodegradable constraints 744 keep protrusion 710 in a constrained state for initial deployment. Protrusion 710 has tines or legs 714 that extend from the anchor 102 and that have pierced the mucosa 803 and the muscle layer 801 of the luminal wall. The use of biodegradable constraints 744 that dissolve in the duodenum over a period of time, e.g. 1-3 months, allows the compound barb protrusion 710 to extend between about 2 mm and about 4 mm from the anchor 102 when placed in the duodenum, and then extend further when the constraints have dissolved. For example, the protrusion 710 may extend to between about 4 mm and 8 mm when released from the constrained state.

FIG. 8D shows implant 700 after remodeling of the tissue and after release of biodegradable constraints 744. As in the case of the conventional barb 810, thickening of the luminal wall has occurred due to the proliferation of tissue around the protrusion 710, including the infiltration of granulation tissue 805 into the mucosa 803. However, release of the constraints 744 allowed protrusion 710 to expand and maintain contact with tough muscle tissue 801 and tough scar tissue that has formed in the muscle layer.

Deployment and Removal of Anchors Secured with Protrusions

Each of the aforementioned implants may be deployed in the intestine, preferably in the duodenum, and more preferably in the duodenal bulb just distal to the pylorus. Typically, a doctor or other qualified person inserts the implant into the intestine with an endoscopic delivery device. During insertion, the delivery device holds the implant in a compressed state. Protrusions of the implant are also held in compressed or constrained state, for example, by a biodegradable constrained. Once in position, the implant is released from the delivery device and allowed to self-expand, causing the protrusions to engage the intestinal wall. In implant with loop and neck protrusions, the expansion of the implant cause each neck coupled to the anchor to push its respective loop against the intestinal wall. Similar, in implants with barbs coupled to the anchor, the expanding anchor causes the barbs to engage the intestinal wall. Some implants may include a sleeve coupled to the anchor, which can be deployed within the intestine as described in U.S. Pat. No. 7,122,058; U.S. Pat. No. 7,329,285; U.S. Pat. No. 7,678,068; and U.S. patent application Ser. No. 11/057,861 (now U.S. Pat. No. 7,837, 633), filed on Feb. 14, 2005, by Levine et al., all of which are incorporated herein by reference in their entireties.

An implant secured with protrusions tipped with open loops or barbs may be removed laparoscopically, surgically, or, more preferably, endoscopically with an endoscope. For example, an implant may be collapsed using a drawstring, then withdrawn from the intestine using an endoscope. Further details on endoscopic removal can be found in U.S. application Ser. No. 11/318,083, filed on Dec. 22, 2005, by Lamport and Melanson; and in U.S. application Ser. No. 12/005,049, filed on Dec. 20, 2007, by Levine et al., both of which are incorporated herein by reference in their entireties.

Seals, Sleeves, and Restrictor Plates

Figure 9B:
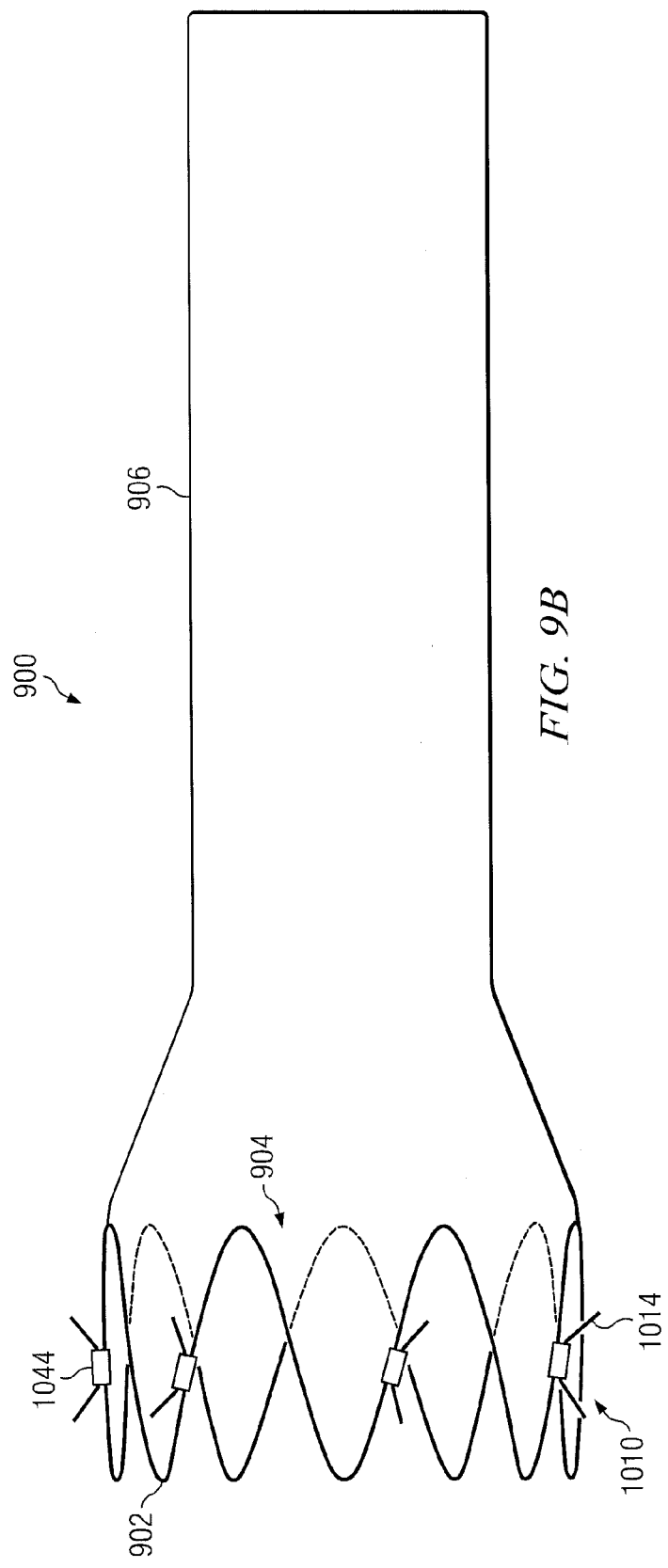
FIG. 9B shows and implant that includes a sleeve extending from an anchor with compound barb protrusions maintained in a constrained state by biodegradable constraints.

FIGS. 9A-9B show an implant 900 that includes an anchor 902 with a polymer covering 904. In the example shown in FIG. 9A, protrusions 910 projecting from the anchor 902 support open loops 912 that can be used to create fibrotic encapsulations in the intestinal wall as described above. Constraints 944, such as biodegradable sutures, maintain protrusions 910 in a constrained state. In the example shown in FIG. 9B, protrusions 1010 projecting from the anchor 902 include compound barbs 1014. Constraints 1044, such as biodegradable tubing, maintain protrusions 1010 in a constrained state. As shown in FIGS. 9A-9B, a sleeve 906 is coupled to the distal side of the anchor 902 for extension into the intestine. The sleeve 906 may be permanently or detachably affixed to the anchor 902. For instance, a detachable sleeve can be endoscopically attached to or removed from a permanently or semi-permanently secured anchor depending on treatment progress.

Typically, the sleeve 906 is floppy and conformable to the wall of the intestine when deployed. It also has a wall thickness of less than about 0.001 inch to about 0.005 inch and a coefficient of friction of about 0.2 or less. The polymer covering 904 and the sleeve 906 may be made of a fluoropolymer, such as ePTFE coated or impregnated with fluorinated ethylene polyethylene (FEP), or any other suitable material. The sleeve 906 and anchor covering 904 can be a single, integrally formed piece. They can also be separate pieces, depending on whether the anchor 902 is partially or wholly uncovered, as long as the anchor 902 forms a sufficiently good seal between the sleeve 906 and the stomach, pylorus, and/or intestine to funnel chyme through the sleeve 906. Each loop 912 or barb 1014 remains uncovered or only partially covered to promote the in-growth of fibrotic tissue.

Anchors secured with loops and necks may also be used to secure restrictor plates within the gastrointestinal tract to treat obesity, such as the restrictor plates disclosed in U.S. patent application Ser. No. 10/811,293, filed on Mar. 26, 2004, by Levine et al.; U.S. patent application Ser. No. 11/330,705, filed on Jan. 11, 2006, by Levine et al.; and U.S. patent application Ser. No. 11/827,674, filed on Jul. 12, 2007, by Levine et al., all of which are incorporated herein by reference in their entireties. An implant with a restrictor plate typically includes a restricting aperture that retards the outflow of food from the stomach to the intestine. The diameter of the aperture is less than 10 mm, is preferably less than 7 mm, and is more preferably initially in the range of about 3-5 mm. Alternatively, the aperture may be elastic and expandable under pressure from material flowing through the anchor and the aperture at elevated physiological pressures; as pressure increases, the aperture opens to greater diameters. The implant may include a sleeve that extends into the intestine.

While this invention has been particularly shown and described with references to example embodiments thereof, it will be understood by those skilled in the art that various changes in form and details may be made therein without departing from the scope of the invention encompassed by the appended claims. For example, all or part of the protrusions described above can be covered to further control interaction with contacting tissue. A bio-absorbable suture or adhesive could be used to affix the covering to the protrusion. As the bio-absorbable material degrades or is absorbed by the body, the covering is free to fan open, creating an added level of control of interaction between the protrusion and the surrounding tissue. Alternatively, the protrusion may be made from a polymer or a composite material, such as a nondegradable or biodegradable material. Implants can also include different types of protrusions, e.g., any combination of straight protrusions with open loops, helical protrusions with open loops, and pointed barbs.

What is claimed is:

1. An implant comprising:
   a cylindrical, collapsible anchor to be deployed within a lumen;
   a protrusion coupled to the anchor, the protrusion, in a constrained state, extending from an exterior surface of the anchor to penetrate tissue and, in an unconstrained state, extending further from the exterior surface of the anchor than in the constrained state, the protrusion including a first segment proximate the anchor that extends from the anchor along a first axis, and a second segment that extends from the first segment along a second axis, the first segment, in the constrained state, being collapsed against the anchor, the first axis aligned with the surface of the anchor, and the second segment, in the constrained state, extending away from the anchor; and
   a biodegradable constraint configured to maintain the protrusion in the constrained state until the constraint releases.

2. The implant of claim 1, wherein the constraint covers at least a portion of the protrusion.

3. The implant of claim 2, wherein the covered portion of the protrusion includes a mid-portion of the protrusion.

4. The implant of claim 2, wherein the constraint further covers at least a portion of the anchor.

5. The implant of claim 4, wherein the constraint includes a tube.

6. The implant of claim 4, wherein the constraint includes a suture that ties a portion of the protrusion to a portion of the anchor.

7. The implant of claim 1, wherein the constraint degrades when exposed to water.

8. The implant of claim 1, wherein the constraint degrades when exposed to acid.

9. The implant of claim 1, wherein the constraint is bioresorbable.

10. The implant of claim 1, further comprising additional biodegradable constraints, each constraint configured to maintain the protrusion in a different constrained state and to degrade over a different predetermined period after the implant has been deployed within the lumen.

11. The implant of claim 1, wherein the protrusion is a bi-directional barb.

12. The implant of claim 11, wherein the barb comprises two tines with ends directed in opposite directions from each other and outwardly from the anchor, of which one tine is so oriented at an oblique angle as to prevent longitudinal movement of the implant in a first direction and another tine is so oriented at an oblique angle as to prevent longitudinal movement of the implant in a second direction substantially opposite to the first direction.

13. The implant of claim 1, wherein the protrusion is coupled to the anchor between ends of the anchor.

14. The implant of claim 1, wherein the protrusion extends between about 4 mm and about 8 mm from the exterior surface of the anchor when released from the constrained state.

15. The implant of claim 1, wherein the protrusion is configured to penetrate a wall of the lumen.

16. The implant of claim 1, wherein the protrusion is formed of wire with a diameter of about 0.010 inches to about 0.040 inches.

17. The implant of claim 1, wherein, in the constrained state, a portion of the protrusion folds against the anchor.

18. The implant of claim 1, wherein, in the constrained state, a portion of the protrusion extends outward from the anchor at an angle of between about 30 degrees and about 50 degrees.

19. The implant of claim 1, wherein, in the constrained state, a portion of the protrusion extends outward from the anchor at an angle of about 41 degrees.

20. The implant of claim 1, wherein, in a relaxed state, a portion of the protrusion extends outward from the anchor at an angle of between about 41 degrees and about 90 degrees.

21. The implant of claim 1, wherein, in a relaxed state, a portion of the protrusion extends outward from the anchor at an angle of about 82 degrees.

22. The implant of claim 1, wherein the protrusion is formed as a unitary piece.

23. The implant of claim 1, wherein:
   the second axis is oriented at an oblique angle to the first axis.

24. The implant of claim 1, wherein, in the constrained state, the protrusion extends between about 2 mm and about 4 mm from the exterior surface of the anchor.

25. The implant of claim 1, wherein the anchor has a relaxed diameter of at least about 40 mm.

26. The implant of claim 1, wherein the anchor is a wave anchor.

27. The implant of claim 1, further comprising:
   an unsupported, thin-walled sleeve coupled to the anchor and configured to extend into the lumen upon deployment of the collapsible anchor.

28. The implant of claim 1, further comprising:
   a drawstring configured to collapse the anchor.

29. The implant of claim 1, wherein, in the constrained state, the protrusion extends at least about 2 mm from the exterior surface of the anchor.

30. An implant comprising:
   a collapsible anchor to be deployed within a lumen;
   a bi-directional barb coupled to the anchor, the barb, in a constrained state, extending from an exterior surface of the anchor to penetrate tissue and, in an unconstrained state, extending further from the exterior surface of the anchor than in the constrained state, the barb including a first segment proximate the anchor that extends from the anchor along a first axis, and a second segment that extends from the first segment along a second axis oriented at an oblique angle to the first axis, the first segment, in the constrained state, being collapsed against the anchor, the first axis aligned with the surface of the anchor, and the second segment, in the constrained state, extending away from the anchor; and
   a biodegradable constraint configured to maintain the barb in the constrained state until the constraint releases.

* * * * *